(12) United States Patent
Winslow et al.

(10) Patent No.: US 8,137,358 B2
(45) Date of Patent: Mar. 20, 2012

(54) METHOD AND APPARATUS FOR POSITIONING AN IMPLANT

(75) Inventors: Nathan A. Winslow, Warsaw, IN (US); Brian Berelsman, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1085 days.

(21) Appl. No.: 12/023,634

(22) Filed: Jan. 31, 2008

(65) Prior Publication Data

US 2008/0119861 A1 May 22, 2008

Related U.S. Application Data

(62) Division of application No. 10/651,793, filed on Aug. 29, 2003, now Pat. No. 7,338,496.

(51) Int. Cl.
*A61F 5/00* (2006.01)

(52) U.S. Cl. .......................................................... 606/87

(58) Field of Classification Search ................ 606/86 R, 606/87, 96, 97, 98, 99
See application file for complete search history.

(56) References Cited

U.S. PATENT DOCUMENTS

| | | | |
|---|---|---|---|
| 2,239,088 A | 4/1941 | Ettinger | |
| 3,067,740 A | 12/1962 | Haboush | |
| 3,530,854 A | 9/1970 | Kearney | |
| 4,012,796 A | 3/1977 | Weisman et al. | |
| 4,234,309 A | 11/1980 | Sellers | |
| 4,337,773 A | 7/1982 | Raftopoulos et al. | |
| 4,357,716 A | 11/1982 | Brown | |
| 4,624,673 A | 11/1986 | Meyer | |
| 4,718,916 A | 1/1988 | Morscher et al. | |
| 4,770,660 A | 9/1988 | Averill | |
| 4,834,080 A | 5/1989 | Brown | |
| 4,896,662 A | 1/1990 | Noble | |
| 4,944,759 A | 7/1990 | Mallory et al. | |
| 4,994,085 A | 2/1991 | Sawai et al. | |
| 5,047,061 A | 9/1991 | Brown | |
| 5,078,746 A | 1/1992 | Garner | |
| 5,080,680 A | 1/1992 | Mikhail et al. | |
| 5,092,892 A | 3/1992 | Ashby et al. | |
| 5,180,395 A | 1/1993 | Klaue et al. | |

(Continued)

FOREIGN PATENT DOCUMENTS

DE 19518391 11/1996

(Continued)

OTHER PUBLICATIONS

Comprehensive® Fracture Stem, Positioning Sleeve Surgical Technique, brochure, 8 pages (2005) Biomet Orthopedics, Inc.

(Continued)

*Primary Examiner* — Anu Ramana
(74) *Attorney, Agent, or Firm* — Harness, Dickey

(57) ABSTRACT

A method for using a jig to position an implant at an implantation site of a bone. The method includes the following: tapping the implantation site using a tapping device; axially threading the jig into the implantation site using an insertion tool; adjusting the position of the jig at the implantation site as necessary by axially rotating the jig relative to the bone; axially and substantially non-rotationally inserting the implant through the jig whereby the implant contacts a substantially smooth interior surface of the jig to support the implant at the implantation site such that the implant does not substantially contact an interior surface of the bone canal at the implantation site; and securing the implant at the implantation site using bone cement.

19 Claims, 4 Drawing Sheets

U.S. PATENT DOCUMENTS

| | | | |
|---|---|---|---|
| 5,201,769 A | 4/1993 | Schutzer | |
| 5,246,459 A | 9/1993 | Elias | |
| 5,282,865 A | 2/1994 | Dong | |
| 5,340,362 A | 8/1994 | Carbone | |
| 5,376,124 A | 12/1994 | Gustke et al. | |
| 5,470,336 A * | 11/1995 | Ling et al. | 606/105 |
| 5,507,831 A | 4/1996 | Burke | |
| 5,507,832 A | 4/1996 | Michielli et al. | |
| 5,554,192 A | 9/1996 | Crowninshield | |
| 5,569,255 A | 10/1996 | Burke | |
| 5,597,383 A * | 1/1997 | Carbone | 128/898 |
| 5,658,351 A | 8/1997 | Dudasik et al. | |
| 5,683,395 A | 11/1997 | Mikhail | |
| 5,693,099 A | 12/1997 | Harle et al. | |
| 5,702,486 A | 12/1997 | Craig et al. | |
| 5,746,771 A | 5/1998 | Clement, Jr. et al. | |
| 5,755,793 A | 5/1998 | Smith et al. | |
| 5,766,262 A | 6/1998 | Mikhail | |
| 5,861,043 A | 1/1999 | Carn | |
| 5,885,295 A | 3/1999 | McDaniel et al. | |
| 5,885,299 A | 3/1999 | Winslow et al. | |
| 5,910,172 A | 6/1999 | Penenberg | |
| 5,925,077 A | 7/1999 | Williamson et al. | |
| 5,951,561 A | 9/1999 | Pepper et al. | |
| 5,984,968 A | 11/1999 | Park | |
| 5,997,581 A | 12/1999 | Khalili | |
| 6,110,175 A | 8/2000 | Scholl | |
| 6,126,691 A | 10/2000 | Kasra et al. | |
| 6,168,627 B1 | 1/2001 | Huebner | |
| 6,168,628 B1 | 1/2001 | Huebner | |
| 6,174,335 B1 | 1/2001 | Varieur et al. | |
| 6,193,758 B1 | 2/2001 | Huebner | |
| 6,251,141 B1 | 6/2001 | Pierson, III et al. | |
| 6,267,785 B1 | 7/2001 | Masini | |
| 6,277,123 B1 | 8/2001 | Maroney et al. | |
| 6,379,391 B1 | 4/2002 | Masini | |
| 6,395,004 B1 | 5/2002 | Dye et al. | |
| 6,494,913 B1 | 12/2002 | Huebner | |
| 6,500,209 B1 | 12/2002 | Kolb | |
| 6,517,581 B2 | 2/2003 | Blamey et al. | |
| 6,652,589 B2 | 11/2003 | Schmotzer et al. | |
| 6,669,734 B2 | 12/2003 | Spotorno et al. | |
| 7,044,978 B2 | 5/2006 | Howie et al. | |
| 7,179,264 B2 | 2/2007 | Cassell | |
| 2002/0045948 A1 | 4/2002 | Schmotzer et al. | |
| 2002/0095217 A1 | 7/2002 | Masini | |
| 2003/0149486 A1 | 8/2003 | Huebner | |
| 2003/0171816 A1 | 9/2003 | Scifert et al. | |
| 2004/0122437 A1 | 6/2004 | Dwyer et al. | |

FOREIGN PATENT DOCUMENTS

| | | |
|---|---|---|
| EP | 0743048 | 11/1996 |
| EP | 1082943 | 3/2001 |
| FR | 2595565 | 9/1987 |
| FR | 2686016 | 7/1993 |
| JP | 2277452 | 11/1990 |
| JP | 5123333 | 5/1993 |
| WO | WO-9301769 | 2/1993 |
| WO | WO-9302641 | 2/1993 |

OTHER PUBLICATIONS

Comprehensive® Positioning Sleeve, brochure, 1 page (2005) Biomet Orthopedics, Inc.

* cited by examiner

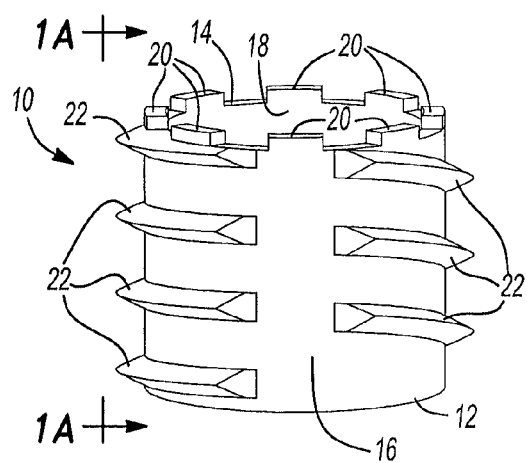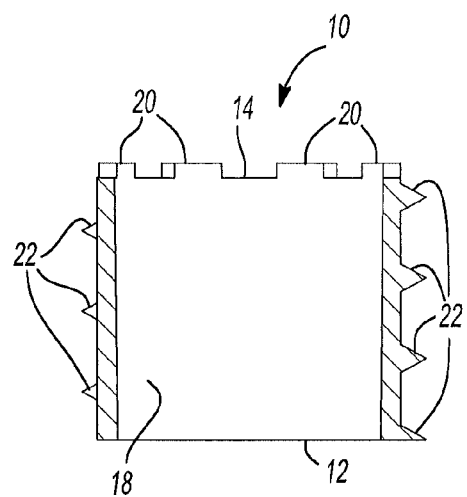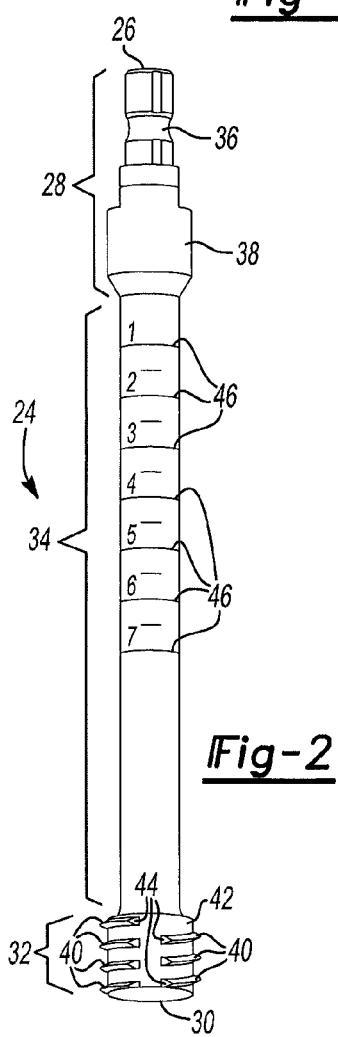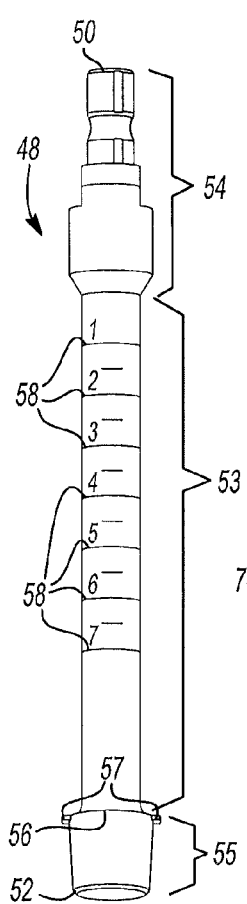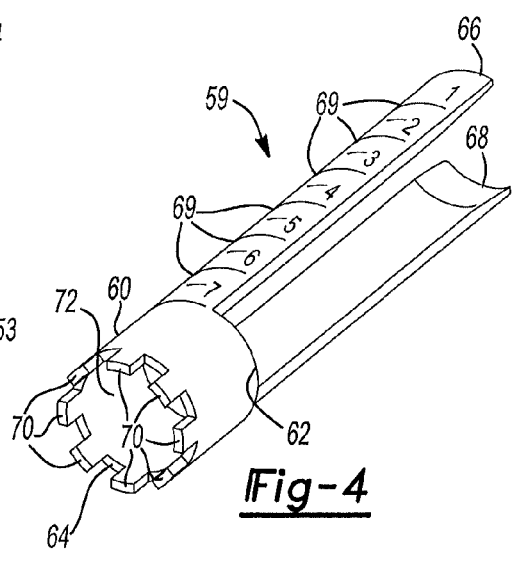
Fig-1
Fig-1A
Fig-2
Fig-3
Fig-4

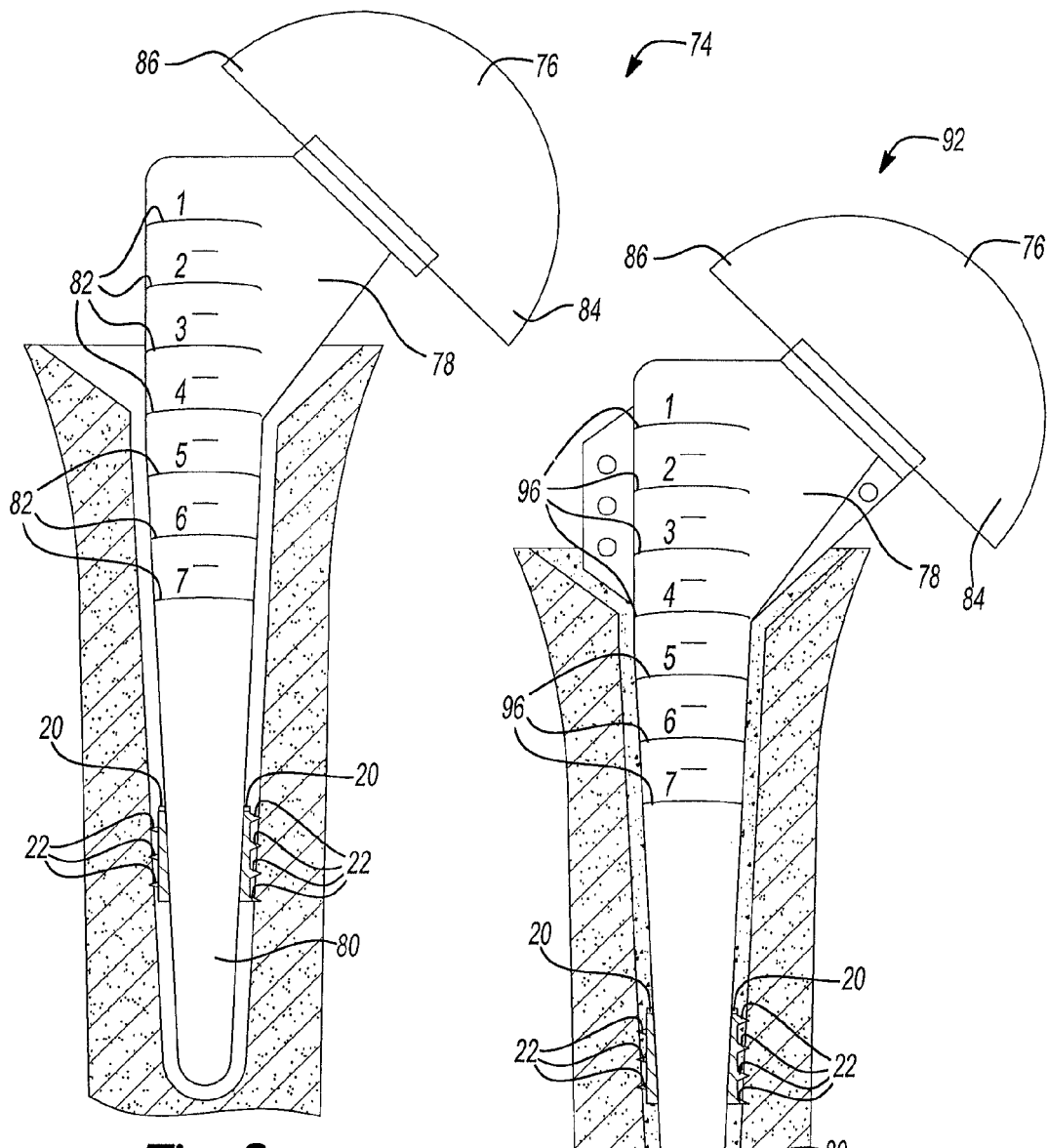

METHOD AND APPARATUS FOR POSITIONING AN IMPLANT

CROSS-REFERENCE TO RELATED APPLICATION

This application is a divisional application of U.S. patent application Ser. No. 10/651,793, filed on Aug. 29, 2003. The disclosure of the above application is incorporated herein by reference.

FIELD OF THE INVENTION

The present invention generally relates to prosthetic implant positioning devices. In particular, the present invention relates to a positioning jig for properly positioning an implant during shoulder arthroplasty for fractures of the proximal humerus.

BACKGROUND OF THE INVENTION

Fractures of the proximal humerus may occur due to injury or weakened bone. Often, the proximal humerus fractures at different points into multiple fragments, such as the greater tuberosity, the lesser tuberosity, the head, and the shaft. Such fractures may require the replacement of the proximal humerus with an implant. The implant generally consists of a head, neck, and stem.

To insure that the implant is properly positioned at the proximal humerus, a positioning jig may be used. Conventional positioning jigs typically engage either an exterior or interior portion of the remaining humerus as well as the trial implant and/or the permanent implant. Such positioning jigs permit joint reduction with the trial as well as use of the jig to position the permanent implant in substantially the same position as the trial.

While current fracture jigs are suitable for their intended uses, they are all subject to improvement. The present invention provides a simplified, easy to use, and efficient fracture jig device, system, and method for positioning both a trial implant and a permanent implant at an injury site.

SUMMARY OF THE INVENTION

The present teachings provide for a method for using a jig to position an implant at an implantation site of a bone. The method includes the following: tapping the implantation site using a tapping device; axially threading the jig into the implantation site using an insertion tool; adjusting the position of the jig at the implantation site as necessary by axially rotating the jig relative to the bone; axially and substantially non-rotationally inserting the implant through the jig whereby the implant contacts a substantially smooth interior surface of the jig to support the implant at the implantation site such that the implant does not substantially contact an interior surface of the bone canal at the implantation site; and securing the implant at the implantation site using bone cement.

The present teachings further provide for a method for using a jig to position an implant at an implantation site of a bone. The method includes the following: analyzing the implantation site to determine the appropriate size and position of the implant; selecting a trial implant that is substantially the same size as the implant, the trial implant having a trial stem and a trial head; referencing a position of an inferior portion of the trial head against score marks on the trial stem, the trial stem is properly positioned at the implantation site when the score mark corresponding to the inferior portion of the trial head is proximate to a reference surface of the bone; preparing the implantation site using a tapping device having a shank with a control surface operable to engage a control device, a cutting implement having a cutting surface, and an elongated shaft connecting the cutting implement to the shank, the elongated shaft having a series of tick marks that are substantially the same as the score marks on the trial stem, preparation of the implantation site includes driving the tapping device into the implantation site to a depth such that a tick mark corresponding to the score mark referenced against the inferior portion of the trial head is proximate to the reference surface of the bone; positioning a jig at the implantation site using an insertion tool, the insertion tool having a series of reference marks that are substantially the same as the score marks and the tick marks and a head operable to mate with the jig, the jig is positioned at the implantation site to a depth such that a reference mark corresponding to the score mark referenced against the inferior portion of the trial head is proximate to the reference surface of the bone; inserting the trial stem into the jig such that the score mark of the trial stem corresponding to the position of the inferior portion of the trial head is proximate to the reference surface of the bone, thereby positioning the trial stem at an optimum height at the implantation site; adjusting the position of the trial stem as necessary by screwing the jig up or down in the implantation site using the insertion tool; and inserting the implant into the jig and securing the implant in position.

The present teachings also provide for a method for using a jig to position an implant in an intramedullary canal of a humerus. The method includes the following: tapping the intramedullary canal using a tapping device; axially threading the jig into the intramedullary canal using an insertion tool; substantially centering the implant in the intramedullary canal by axially inserting the implant through both a first end of the jig having a first diameter and a second end of the jig that is opposite to the first end and has a second diameter that is smaller than the first diameter, whereby the implant contacts a substantially smooth inner surface of the jig; adjusting the height of the jig in the intramedullary canal as necessary so that a point on a stem of the implant aligned with an inferior portion of a head of the implant is proximate to an exterior reference surface of the humerus when the implant is seated in the jig; and securing the implant in the intramedullary canal using bone cement.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of a jig illustrated in accordance with an embodiment of the present invention;

FIG. 1a is cross-sectional view of the jig of FIG. 1 taken along line 2-2 of FIG. 1;

FIG. 2 is a perspective view of a tapping device used to prepare the humerus to receive the jig of FIG. 1;

FIG. 3 is a perspective view of an insertion device operable to insert the jig of FIG. 1 within the humerus;

FIG. 4 is a perspective view of an alternative insertion device operable to insert the jig of FIG. 1 within the humerus;

FIG. 8 is a side cross-sectional view of the jig of FIG. 1 seated within the humerus, the jig holding a trial proximal humeral implant within the humerus to permit reduction of the trial joint;

FIG. 9 is a side cross-sectional view of the jig of FIG. 1 seated within the humerus, the jig holding a permanent proximal humeral implant in at least substantially the same position as the trial implant of FIG. 8.

DETAILED DESCRIPTION OF THE PREFERRED EMBODIMENTS

Figure 7:
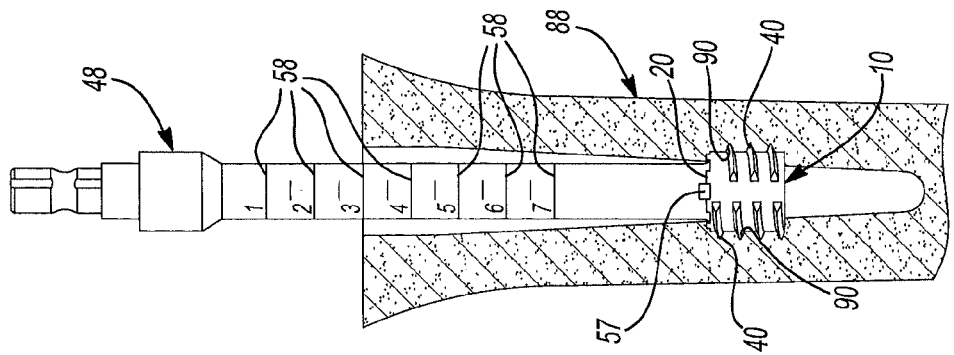
FIG. 7 is a side view of the insertion device of FIG. 3 inserted within the prepared proximal humerus of FIG. 6 to implant the jig of FIG. 1 within the humerus.

The following description of the embodiments is merely exemplary in nature and is in no way intended to limit the invention, its application, or uses. While the invention is described below as a positioning device, system, and method for a humeral implant, the invention may be used to properly position a variety of different bony and non-bony implants in both human and non-human patients. Further, while the invention is described as a fracture jig, the invention may be used to trial and/or retain an implant regardless of whether a fracture has actually occurred.

A jig in accordance with an embodiment of the present invention is illustrated in FIGS. 1 and 1a at 10. As illustrated, the jig 10 generally takes the form of a closed circular sleeve that is a single integral unit. However, the illustration of jig 10 at FIG. 1 is for demonstrative purposes only as the jig 10 may be an open circular or non-circular sleeve comprised of a single unit or multiple parts. The jig 10 generally includes a first end 12, a second end 14, an exterior surface 16, and an interior surface 18.

The second end 14 of the jig 10 includes at least one detail 20. As illustrated, the detail 20 is a projection that extends from the second end 14. However, the detail 20 may be a recess within the second end 14 or may be any other suitable engagement surface to permit engagement between the jig 10 and a suitable implantation tool, discussed in detail below. For example, detail 20 does not need to be located at the second end 14 and may be a projection located on the interior surface 18 that engages flutes on the stem of an implant and/or insertion tool.

The exterior surface 16 optionally includes at least one extension or rib 22. The ribs 22 project from the exterior surface 16 and extend in a circular, stepwise fashion or in any other manner about the exterior surface 16. The ribs 22 may be of various shapes and sizes, but are configured for receipt by corresponding depressions at an implantation site. Any other type of retention feature to retain the jig 10 may also be used, such as threads or an annular feature. As illustrated, the ribs 22 do not extend continuously about the exterior surface 16. However, FIGS. 1 and 1a are for demonstrative purposes only and the ribs 22 may extend about the exterior surface 16 in either a continuous or non-continuous configuration. The ribs 22 may be angled to decrease the force required to implant the jig 10 and/or make the jig 10 self-tapping. In addition to, or in place of, providing angled ribs 22, the first end 12 and/or the exterior surface 16 may optionally include various other features to make the jig 10 self-tapping.

With particular reference to FIG. 1a, the interior 18 of the jig 10 is open at both the first end 12 and the second end 14 to receive and hold any suitable implant. Alternatively, the jig 10 may be opened at one end to receive the distal most portion of the implant. To better secure the implant within the interior 18, the interior 18 may be tapered from the second end 14 to the first end 12 with the second end 14 having a greater diameter than the diameter of the first end 12. The taper of the interior 18 may substantially match the taper of the stem of a typical implant inserted within the interior 18. Alternatively, any other type of suitable engagement surface may also be employed. For example, interior 18 may include an internal feature that acts as a stop or locating device for receiving an implant.

The overall size of the jig 10 may vary depending upon the dimensions of the site that it is to be implanted at. Further, the jig 10 may be available in various different lengths and widths. Still further, the diameter of the interior 18 of the jig 10 may also vary, depending upon both the dimensions of the implantation site and the dimensions of the implant to be received by the interior 18. The diameter of the interior 18 may vary together with, or apart from, changes in the overall size of the jig 10.

The jig 10 may be made from a variety of suitable materials. It is preferred that the jig 10 be made from polymethylmethacrylate. However, any suitable plastic, bone cement, resorbable material, or biocompatible non-resorbable material may be used.

FIG. 2 illustrates a tapping device at 24. The tapping device 24 generally comprises a first end 26 having a shank 28, a second end 30 having a cutting implement 32, and an elongated shaft 34 that connects the first end 26 to the second end 30.

The shank 28 is any typical shank operable to permit control of the tapping device 24 by a suitable instrument, such as a T-handle (not shown). As illustrated, the shank 28 has a recessed control surface 36 for cooperation with, for example, the T-handle and a collar 38 that acts as a stop to prevent the tapping device 24 from drilling to far within the implantation site. The shape and configuration of the shank 28 may vary to permit cooperation with different control instruments, in addition to, or instead of, the T-handle.

The cutting implement 32 comprises a series of ribs 40 that extend from an outer surface 42. The ribs 40 extend about the implement 32 in a stepped, spiral orientation. As illustrated, the ribs 40 do not extend around the outer surface 42 in a continuous manner, but are instead interrupted at the same interval in each rib 40. However, it must be noted that in particular applications the ribs 40 may be configured to extend continuously about the implement 32. The ribs 40 include leading edges 44 that may be angled to assist in cutting and chipping bone of the implantation area to create threads at the implantation area. It must be noted that this description of the ribs 40 is merely exemplary as the ribs 40 may be of a variety of different design configurations.

The elongated shaft 34 optionally includes a series of score marks 46. The score marks 46 are positioned at regular intervals along the shaft 34. The score marks 46 may include a series of dashes, numbers, letters, or any combination thereof. The score marks 46 may extend the length of the shaft 34 or only a portion of the shaft 34.

With reference to FIG. 3, an inserter for implanting the jig 10 is illustrated at 48. The inserter 48 generally comprises a first end 50, a second end 52 opposite the first end 50, and an intermediary portion 53 that connects the first end 50 to the second end 52. The first end 50 has a shank 54 that is substantially similar to the shank 28 of the tapping device 24. The description of the shank 28 above also applies to the shank 54, thus making it unnecessary to include a description of the shank 54 here.

The second end 52 comprises a head 55 defined, in part, by the second end 52 and an upper head region 56. The head 55 may be of different sizes depending on the size of the jig 10. The second end 52 is tapered inward, toward an interior of the inserter 48, at its terminus. The upper head region 56 includes at least one engagement surface 57. The engagement surface 57 may be an extension as illustrated or may be a recess located within the upper head region 56.

The intermediary portion 53 is longer, by approximately 10 mm, than the elongated shaft 34. The intermediary portion 53 may include a series of score marks 58. The score marks 58 may be any suitable reference markings, such as numbers or letters. The score marks 58 are positioned at intervals that are at least substantially equal to the score marks 46 of the tapping device 24. The score marks 58 may extend from the shank 54 to a distance down the intermediary portion 53 substantially equal to a distance that the score marks 46 extend from shank 28.

FIG. 4 illustrates an inserter 59 according to a second embodiment. The inserter 59 generally comprises a main body 60, a first end 62, and a second end 64 opposite the first end 62. Extending from the first end 62 is a first handle 66 and a second handle 68. Both the first handle 66 and the second handle 68 include score marks 69 that are substantially the same as the score marks 58 of inserter 48. The second end 64 includes a jig engagement detail 70. The jig engagement detail 70 may be a tab that extends from the second end 64 as illustrated, or may be a recess within the second end 64. Extending through the main body 60 is an inner region 72. Generally, the diameter of the inner region 72 is tapered from the first end 62 to the second end 64 and is at least as large as the interior 18 of the jig 10. The inserter 59 may be of various different sizes depending on the size of the jig 10.

Figure 5:
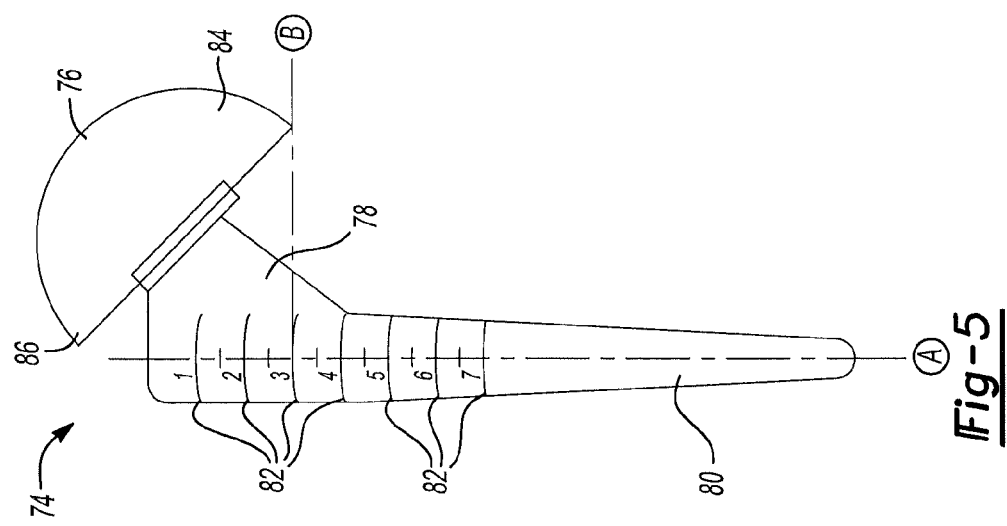
FIG. 5 is a side view of a trial humeral implant.

FIG. 5 illustrates a trial implant at 74. While the trial implant 74 is illustrated as a trial humeral implant, the trial implant 74 may be any suitable bony or non-bony implant. The trial humeral 74 is generally comprised of a head 76, a neck 78, and a stem 80. The stem 80 includes a series of score marks 82. The score marks 82 are generally positioned at uniform intervals along the stem 80 and are typically either letters or numbers. The trial humeral 74 has a vertical reference line A that extends through the stem 80 and at least a portion of the neck 78. A horizontal reference line B extends from a inferior portion 84 of the head 76, which is at an opposite end of the head 76 from a superior portion 86, to one of the score marks 82.

The trial humeral 74 may be of various different shapes and sizes depending upon the dimensions of the implantation site. In particular, the head 76 may be of different dimensions, with the particular score mark 82 being referenced by the intersection of reference lines A and B being different depending on the size of the head 76. For example, if the head 76 is larger than illustrated, the inferior portion 84 will extend further along the stem 80, thus causing the horizontal reference line B to reference a score mark 82 that is further down the stem 80.

With additional reference to FIGS. 6 through 9 and continued reference to FIGS. 1 through 5, the implantation and operation of the jig 10 will now be described in detail. The description details the implantation of the jig 10 within a fractured humerus 88 to position both the trial humeral implant 74 and a permanent humeral implant that replaces a proximal portion of the humerus 88, including the humeral neck and head (not shown). However, the jig 10 may be implanted in any suitable bony or non-bony surface to position a variety of different implants.

Before the jig 10 is implanted within the fractured humerus 88, the fractured humerus 88 is analyzed by a physician, using conventional techniques, to determine what size trial 74, and specifically what size trial head 76, is required. Once the proper size is determined, the trial head 76 is secured to the neck 78 and the position of the inferior portion 84 of the head 76 is referenced upon the score marks 82 using the point where horizontal reference line B intersects vertical reference line A. The point where reference lines A and B intersect is carefully noted for further use during the implantation process. The size of the trial 74 chosen also has a bearing on the size of the jig 10 used to support the trial 74 and the permanent implant.

Figure 6:
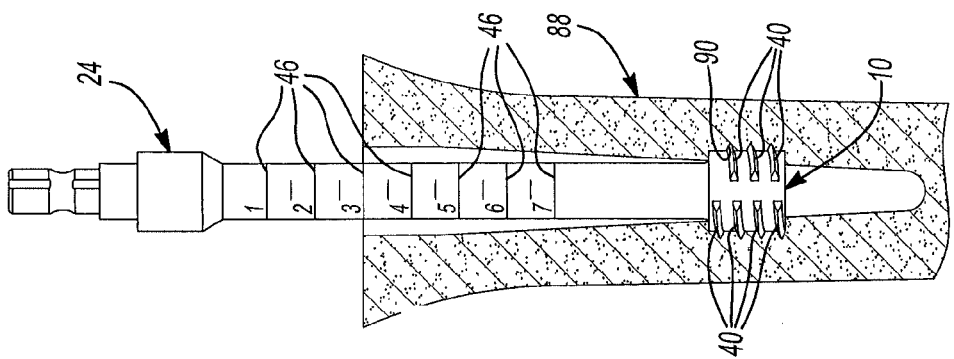
FIG. 6 is a side view of the tapping device of FIG. 1 inserted within a proximal humerus to prepare the humerus for receipt of the jig of FIG. 1.

If the jig 10 is not a self tapping jig, the fractured humerus 88 may be tapped to receive the jig 10. With reference to FIG. 6, to tap the humerus 88, the tapping device 24 is driven within the intact portion of the fractured humerus 88. The tapping device 24 is rotated as it is driven so that the ribs 40 create corresponding grooves 90 within the humerus 88. If the fracture occurs at the medial/inferior intersection of the humeral head and shaft, the tapping device 24 is driven within the humerus 88 until the particular score mark 46 referenced by the intersection of lines A and B on the trial humeral implant 74 is at the surface of the fractured humerus 88, as illustrated in FIG. 6. However, if the fracture is distal to the intersection of the head and shaft, the jig 10 is driven less deeply within the humerus 88.

The score marks 46 on the tapping device 24 and the score marks 82 on the trial implant 74 are calibrated such that when the tapping device 24 is driven within the humerus 88 to a depth such that the score mark 46 corresponding to the score mark 82 at the intersection of reference lines A and B of the trial humeral 74 is at the surface of the fractured humerus 88. The depth of the grooves 90 created by the tapping device 24 are at approximately the proper depth of the jig 10 required to support the trial humeral implant 74, and a permanent humeral implant, in the proper position. However, since the tapping device 24 is generally longer than the inserter 48, the grooves 90 will be of an added depth so that the jig 10 may be driven deeper if necessary.

With reference to FIG. 7, after the humerus 88 is tapped, the inserter 48 is used to implant the jig 10 within the humerus 88. The jig 10 mates with the inserter 48 through cooperation between the engagement surfaces 57 and surfaces between details 20 of the jig 10 when the head 55 is seated within the interior 18 of the jig 10. The inserter 48 is driven within the tapped humerus 88 to a depth such that the score mark 58 of the inserter 48, which is equivalent to the score mark 82 of the trial 74 referenced by the intersection of reference lines A and B, is positioned at the surface of the humerus 88. Driving the inserter 48 to this depth places the jig 10 within the grooves 90 and at an approximate depth to support the trial humeral implant 74 at the correct height.

Alternatively, the inserter 59 may be used to insert the jig 10 within the humerus 88. The inserter 59 engages the jig 10 through cooperation between the sleeve engagement detail 70 and surfaces between details 20 of the jig 10. Using the handles 66 and 68, the jig 10 is driven within the humerus until the score mark 69 corresponding to the score mark 82 referenced on the trial 74 is positioned at the surface of the humerus 88. This is done by placing the inserter 59 over the stem 80 of the trial 74 or the stem of a permanent implant 92 (FIG. 9).

With reference to FIG. 8, after the jig 10 is implanted the trial humeral replacement implant 74 is placed within the humerus 88 such that the stem 80 is seated within the interior 18 of the jig 10. Specifically, the tapered stem 80 is inserted within the tapered interior 18 of the jig 10 until the diameter of the stem 80 becomes the same as or larger than the interior 18 of the jig 10, thus preventing the implant 74 from being inserted further within the jig 10 and humerus 88. The jig 10 supports the trial implant 74 within the humerus 88 to create a substantially even cavity between the trial humeral 74 and the humerus 88 to receive bone cement once the permanent implant 92 is in position.

With the trial humeral 74 supported within the humerus 88 by the jig 10, the humeral joint is reduced. If the trial humeral 74 is not at the correct height, the inserter 48 may be used to adjust the jig 10 accordingly. If the inserter 59 is used, the inserter 59 may remain secured to the jig 10 during the reduction processes because the trial humeral 74 may be inserted through the inner region 72 of the inserter 59. The jig 10 may then be adjusted using the inserter 59 without removing the trial 74.

With reference to FIG. 9, after the trial humeral 74 is properly positioned, it is replaced with the permanent implant 92. Because the dimensions of the permanent implant 92 are substantially similar to the dimensions of the trial humeral 74, when the permanent implant 92 is seated within the interior 18 of the jig 10, it will be in substantially the same position as the trial humeral 74 was. Because the permanent implant 92 is substantially similar to the trial humeral 74, the permanent implant 92 need not be described in detail. As with the trial implant 74, support of the permanent implant 92 within the humerus 88 forms a substantially even cement mantle between the permanent implant 92 and the humerus 88 and prevents the permanent implant 92 from contacting the humerus 88. Before the permanent implant 92 is supported by the jig 10 in proper position, bone cement 94 is introduced within the humerus 88 and later hardens within the mantle formed between the implant 92 and the humerus 88 to affix the implant 92 within the humerus. The permanent implant 92 may be provided with reference marks 96, which are similar to the marks 82 of the trial 74, to insure that the permanent implant 92 is in relatively the same position as the trial 74.

Figure 10:
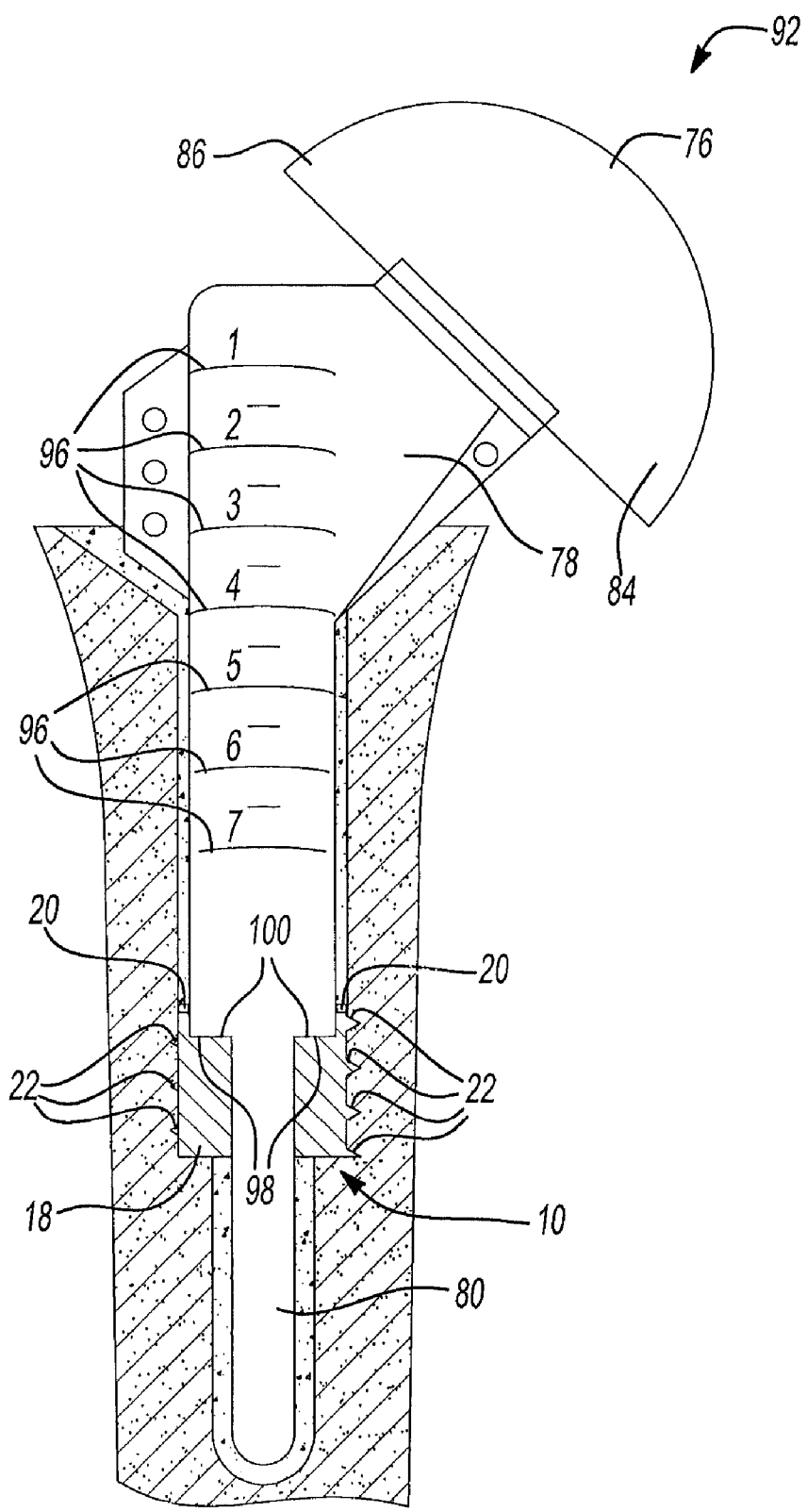
FIG. 10 is a side cross-sectional view of a jig illustrated in accordance with an alternate embodiment of the present invention, the jig seated within the humerus and holding a permanent proximal humeral implant.

The above description is meant to encompass various additional embodiments of the present invention. For example, with reference to FIG. 10, the interior 18 of the implant 10 may have parallel sidewalls. Further the implant 10 may have a receiving surface 98 operable to receive the trial implant 74 and the permanent implant 92, as illustrated. The receiving surface 98 may be any suitable surface or detail operable to mate with a corresponding stop surface or detail, such as stop surface 100, of the trial implant 74 or the permanent implant 92, as illustrated. In the exemplary embodiment of FIG. 10, the receiving surface 98 is a recessed surface of the interior 18 proximate to the second end 14 and the stop surface 100 is a stepped surface of the stem 80.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for using a jig to position an implant at an implantation site of a bone comprising:
   tapping the implantation site using a tapping device;
   axially threading the jig into the implantation site using an insertion tool;
   adjusting the position of the jig at the implantation site as necessary by axially rotating the jig;
   axially and substantially non-rotationally inserting the implant through the jig whereby the implant contacts a substantially smooth interior surface of the jig to support the implant at the implantation site such that the implant does not substantially contact an interior surface of the bone canal at the implantation site; and
   securing the implant at the implantation site using bone cement.

2. The method of claim 1, wherein the implantation site includes an intramedullary canal of a humerus; and
   wherein inserting the implant through the jig substantially centers the implant in the intramedullary canal.

3. The method of claim 2, further comprising inserting and securing the implant in the intramedullary canal such that a first reference mark on a stem of the implant is proximate to an exterior reference surface of the humerus;
   wherein the first reference mark is at an intersection of a longitudinal axis of the stem of the implant and a reference line that extends from an inferior portion of a head of the implant to the longitudinal axis, the reference line intersects the longitudinal axis of the stem substantially at a right angle;
   wherein the implantation site is tapped to a depth in the intramedullary canal such that a second reference mark on the tapping device is at the exterior reference surface of the humerus; and
   wherein the jig is axially threaded, using the insertion tool, to a depth in the intramedullary canal such that a third reference mark on the insertion tool is at the exterior reference surface of the humerus.

4. The method of claim 3, wherein the second reference mark and the third reference mark identify substantially the same position on the tapping device and the insertion tool respectively.

5. The method of claim 3, wherein a plurality of the first reference marks, the second reference marks, and the third reference marks are arranged at substantially equal intervals.

6. The method of claim 1, further comprising selecting the implant from a plurality of implants of different sizes and selecting the jig from a plurality of jigs of different sizes.

7. The method of claim 1, wherein the implant is inserted through an interior of the jig defined by a cylindrical sidewall that is tapered from a first end to a second end.

8. The method of claim 1, wherein the implant is inserted through the jig such that the implant extends through a first end of the jig and a second end of the jig that is opposite to the first end.

9. The method of claim 1, wherein the implant is inserted through the jig until a stop surface of the implant contacts a receiving surface of the jig that is substantially perpendicular to parallel sidewalls of the jig.

10. A method for using a jig to position an implant at an implantation site of a bone comprising:
   analyzing the implantation site to determine the appropriate size and position of the implant, and selecting a reference surface of the bone at the implantation site for reference during positioning of the implant;
   selecting a trial implant that is substantially the same size as the implant, the trial implant having a trial stem and a trial head;
   referencing a position of an inferior portion of the trial head against one of a plurality of score marks on the trial stem, the trial stem is properly positioned at the implantation site when the score mark corresponding to the inferior portion of the trial head is proximate to the reference surface of the bone;

preparing the implantation site using a tapping device having a shank with a control surface operable to engage a control device, a cutting implement having a cutting surface, and an elongated shaft connecting the cutting implement to the shank, the elongated shaft having a series of tick marks that correspond to the score marks on the trial stem, preparation of the implantation site includes driving the tapping device into the implantation site to a depth such that a tick mark corresponding to the score mark referenced against the inferior portion of the trial head is proximate to the reference surface of the bone;

positioning a jig at the implantation site using an insertion tool, the insertion tool having a series of reference marks that correspond to the score marks and the tick marks and a head operable to mate with the jig, the jig is positioned at the implantation site to a depth such that a reference mark corresponding to the score mark referenced against the inferior portion of the trial head is proximate to the reference surface of the bone;

inserting the trial stem into the jig such that the score mark of the trial stem corresponding to the position of the inferior portion of the trial head is proximate to the reference surface of the bone, thereby positioning the trial stem at an optimum height at the implantation site;

adjusting the position of the trial stem as necessary by screwing the jig up or down in the implantation site using the insertion tool; and inserting the implant into the jig and securing the implant in position.

11. The method of claim 10, wherein the implantation site includes an intramedullary canal of a humerus; and wherein inserting the implant through the jig substantially centers the implant in the intramedullary canal.

12. The method of claim 10, wherein the implant is inserted through an interior of the jig defined by a cylindrical sidewall that is tapered from a first end to a second end.

13. The method of claim 10, wherein the implant is inserted through the jig such that the implant extends through a first end of the jig and a second end of the jig that is opposite to the first end.

14. A method for using a jig to position an implant in an intramedullary canal of a humerus comprising:

selecting an exterior reference surface of the humerus for reference during positioning of the implant;

tapping the intramedullary canal using a tapping device;

axially threading the jig into the intramedullary canal using an insertion tool;

substantially centering the implant in the intramedullary canal by axially inserting the implant through both a first end of the jig having a first diameter and a second end of the jig that is opposite to the first end and has a second diameter that is smaller than the first diameter, whereby the implant contacts a substantially smooth inner surface of the jig;

adjusting the position of the jig in the intramedullary canal as necessary so that a point on a stem of the implant aligned with an inferior portion of a head of the implant is proximate to the exterior reference surface of the humerus when the implant is seated in the jig; and securing the implant in the intramedullary canal using bone cement.

15. The method of claim 14, wherein the intramedullary canal is tapped to a depth such that a tick mark on the tapping device is at the exterior reference surface of the humerus, the tick mark corresponds to a score mark on the stem of the implant that is at the point on the stem that is aligned with the inferior portion of the head of the implant.

16. The method of claim 14, wherein the jig is axially threaded into the intramedullary canal such that a reference mark of the insertion tool is at the exterior reference surface of the humerus, the reference mark corresponds to the score mark.

17. The method of claim 14, wherein the jig is selected from a plurality of jigs having different sizes.

18. The method of claim 14, wherein the implant is selected from a plurality of implants of different sizes.

19. The method of claim 14, further comprising substantially centering a trial implant in the intramedullary canal by axially inserting the trial implant through both the first end of the jig and the second end of the jig; and adjusting the position of the jig in the intramedullary canal as necessary so that a reference mark on a stem of the trial implant aligned with an inferior portion of a head of the trial implant is proximate to the exterior reference surface.

* * * * *